United States Patent [19]

Baker et al.

[11] 4,445,641

[45] May 1, 1984

[54] CONTROLLED-RELEASE DISPENSER

[75] Inventors: Richard W. Baker, Bend, Oreg.; Yasuo Ninomiya, Osaka, Japan

[73] Assignee: Bend Research, Inc., Bend, Oreg.

[21] Appl. No.: 338,166

[22] Filed: Jan. 8, 1982

[51] Int. Cl.³ .......................... A01M 1/00; A61L 9/04
[52] U.S. Cl. .......................................... 239/6; 43/900; 239/56
[58] Field of Search ................... 239/6, 53, 55, 56, 57, 239/34, 60; 422/123; 43/131, 132 R

[56] References Cited

U.S. PATENT DOCUMENTS 3,770,199 11/1973 Hoek et al. ..................... 239/55 X
4,356,969 11/1982 Obermayer et al. ............. 239/56 X

*Primary Examiner*—Andres Kashnikow
*Attorney, Agent, or Firm*—Chernoff, Vilhauer, McClung, Birdwell & Stenzel

[57] ABSTRACT

A dispenser for active ingredients is disclosed which provides zero-order rate of release of essentially all of the active ingredients. The dispenser comprises a rate-controlling membrane and a solid microporous polymeric reservoir having interconnected or continuous pores capable of retaining the active ingredient by capillary forces, the reservoir being such that the active ingredient is essentially insoluble therein.

12 Claims, No Drawings

CONTROLLED-RELEASE DISPENSER

BACKGROUND OF THE INVENTION

Devices useful for the controlled release of active ingredients are known and generally comprise a membrane which controls the rate of release and some type of carrier in which the active ingredient is either soluble or partially soluble and thus permeable to the passage of the drug. See, for example, U.S. Pat. Nos. 4,161,283, 3,993,072 and 3,926,188. The principal problems with all of the prior art, including the dispensers of the patents mentioned, are that they cannot maintain a zero-order rate of release over the entire life of the dispensation while at the same time dispensing virtually all of the active ingredient.

A zero-order release rate is an essentially constant rate of release of active ingredient that is independent of the amount of the active ingredient and its vapor pressure and is often of critical importance in the delivery of a given active ingredient; for example, the delivery of pheromones as insect attractants is not effective unless the rate of delivery is within certain very narrow limits. To the extent all of the active ingredient is not dispensed, there is a substantial waste and consequent expense inasmuch as the active ingredient is often quite expensive and the remainder simply must be thrown away with the dispenser.

What is needed therefore, is a controlled-release dispenser which is capable of delivering essentially all of an active ingredient at a selected zero-order rate of release over a broad range of release rates which is inexpensive and easy to fabricate.

These and other objects are accomplished by the controlled-release dispenser of the present invention which is summarized and particularly described below.

SUMMARY OF THE INVENTION

According to the present invention, there is provided a controlled-release dispenser of active ingredients capable of dispensing essentially all of the active ingredient at a selected zero-order rate of release over a broad range of release rates comprising a solid microporous polymeric reservoir with interconnected or continuous pores and a release-rate-controlling membrane, the reservoir being such that the active ingredient is essentially insoluble therein and having pores of appropriate diameter to retain the active ingredient therein by capillary action.

DETAILED DESCRIPTION OF THE INVENTION

The microporous reservoir portion of the controlled-release dispenser of the present invention is formulated preferably from microporous polysulfones, nylons, polycarbonate, polyvinylidene chloride, polyvinylidene fluoride, polytetrafluoroethylene, cellulose esters, regenerated cellulose, polyolefins, polyurethanes, crosslinked polyvinyl alcohols, epoxy resins and polyvinyl chlorides having pores appropriate in size to retain the active ingredient (in liquid or solid form) in the reservoir by capillary action. In the case of solid active ingredients, the solid is transformed into a liquid by melting or by dissolving in a solvent, and this liquid is retained by the porous reservoir by capillary action until it solidifies. In this manner, the only forces retaining the active ingredient in the reservoir are physical, as opposed to chemical, as in prior art dispensers, such as disclosed in U.S. Pat. No. 3,926,188 in which the active ingredient is soluble in a substantially imperforate reservoir matrix, allowing it to diffuse to the reservoir surface. The portion of the active ingredient which is soluble in the reservoir matrix cannot be released at zero-order.

The release rate of the active ingredient through the rate-controlling membrane can be conveniently adjusted to the desired value by techniques known in the art including varying the surface area, thickness, and composition of the membrane. Exemplary materials for fabricating the polymeric membrane include polyethylene; polypropylene; ethylene/vinyl acetate copolymers; silicone rubbers; neoprene rubber; chlorinated polyethylene; polyvinyl chloride; vinyl chloride copolymers with vinyl acetate, vinylidene chloride, ethylene, and propylene; polyethylene terephthalate; butyl rubber; epichlorohydrin rubbers; ethylene/vinyl alcohol copolymers; polystyrene/acrylonitrile copolymers; polyamides; polyurethanes; polyesters; and the like.

The invention is particularly useful for the controlled release of very expensive active ingredients, liquid or solid, such as pheromones, juvenile hormones, fragrances, perfumes, insecticides, fumigants, deodorizers, insect attractants and repellants, animal attractants and repellents, and pharmaceutical and veterinary drugs.

The invention is particularly useful for the controlled release of liquid active ingredients. Controlled-release dispensers that contain liquids are difficult to fabricate without a solid reservoir. The use of microporous reservoirs that hold the active ingredient by capillary action thus enables easy fabrication of dispensers of liquid active ingredients.

Some active ingredients are sensitive to degradation by oxidation or by ultraviolet light, and must be protected in order to provide long-term action. The invention is particularly useful for providing such protection. If the active ingredient is photosensitive or especially susceptible to rapid oxidation, the reservoir or the rate-controlling membrane may contain additives such as ultraviolet light absorbers and antioxidants.

The dispenser may have a portion of its outer surface covered with an impermeable backing material so as to cause the active ingredient to be released, in the case of a disc shape, from one side only. A suitable impermeable backing film is a polyethylene-foil-paper laminate made by Lithotype Co. of South San Francisco, Calif. In some cases, as in the case of a polyurethane rate-controlling membrane, the polyethylene-side backing of the film must first be coated with an adhesive such as Elvax 40 made by DuPont.

EXAMPLES

Generally disc-shaped controlled-release dispensers of the present invention were made by heat sealing the rate-controlling membrane to the polyethylene side of an impermeable backing material comprising a polyethylene/foil/paper laminate with a disc of the microporous reservoir material inserted therebetween, the reservoir having been impregnated with the active ingredient. The specifications of the dispensers, including sizes, component materials and active ingredients are set forth in Table I. All active ingredients shown are pheromones, insect attractants or fragrances. All exhibited zero-order rates of release of essentially all of the active ingredient over periods of time ranging in duration from 40 to 220 days.

Microporous reservoirs of polysulfone are made in the following manner. A 10% by weight solution of polysulfone (Union Carbide P-3500) in dimethyl formamide (DMF) is made. This solution may be cast 20-50 mils thick on a drum or glass plate according to known techniques. The drum or plate is then immediately immersed in a room-temperature water bath, which precipitates the polysulfone, thus forming the microporous reservoir material. The polysulfone sheet is dried at approximately 110° C. for an hour. Individual reservoirs may be cut from the sheet with a circular punch. Reservoirs of polycarbonate, polyvinylidene fluoride and others are formed in a similar fashion.

Microporous reservoirs of polyurethane, cellulose acetate, polyamides, and polytetrafluoroethylene are available from commercial sources and are easily fabricated by conventional techniques known in the art.

In some cases, the release rate of the active ingredient is sufficiently high that a substantial amount of active ingredient must be used, and a large-volume dispenser is required. Large-volume dispensers were made by two methods. In the first method, dispensers were made in the manner set forth above except that a polyethylene ring was used to surround the reservoir, and the membrane and the backing were heat-sealed to the ring. In the second method, a polyethylene or polypropylene cup was used as an impermeable container for the reservoir and active agent, and the membrane was sealed to the top edge of the cup.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

TABLE I

| Reservoir Material | Rate Controlling Membrane | Active Ingredient | Reservoir Volume ($\mu l$) | Membrane Surface Area ($cm^2$) | Release Rate ($\mu g/day$) | Duration of Release (days) |
|---|---|---|---|---|---|---|
| Polysulfone | Polyurethane | (E)-11-tetradecenal | 60 | 2.0 | 45 | 140 |
| Polysulfone | High-density polyethylene | (Z)-9-dodecenyl acetate | 60 | 2.0 | 9 | 220 |
| Polysulfone | Polyamide | (Z)-7-dodecenyl acetate | 130 | 4.9 | 25 | 200 |
| Polysulfone | Low-density polyethylene | (Z)-7,8-epoxy-octadecane | 15 | 0.8 | 15 | 170 |
| Cellulose acetate | Polyurethane | (Z)-7-dodecenyl acetate | 100 | 4.0 | 240 | 50 |
| Cellulose acetate | Polyamide | (E,E)-8,10-dodecadienol | 100 | 4.0 | 35 | 40 |
| Polyvinylchloride | Polyurethane | (Z,E)-9,12-tetradecadienyl acetate | 100 | 4.0 | 30 | 40 |
| Polytetrafluoroethylene | Polyurethane | (Z,E)-7,11-hexadecadienyl acetate | 100 | 4.0 | 10 | 50 |
| Polytetrafluoroethylene | Polyurethane | Gossyplure | 100 | 4.0 | 15 | 50 |
| Polyurethane | Low-density polyethylene | Methyl eugenol | 2500 | 5.1 | 4000 | 110 |
| Polyurethane | High-density polyethylene | Trimedlure | 2500 | 5.1 | 1400 | 130 |
| Polysulfone | High-density polyethylene | Sassafras oil | 150 | 4.9 | 280 | 170 |

What is claimed is:

1. A controlled-release dispenser capable of dispensing essentially all of an active ingredient at a zero-order rate of release comprising a membrane controlling the rate of release of said active ingredient by diffusion through said membrane and a microporous reservoir material which is highly permeable to said active ingredient and in which said active ingredient is essentially insoluble, said microporous reservoir material having interconnected pores capable of retaining said active ingredient by capillary forces.

2. A controlled-release dispenser capable of dispensing essentially all of an active ingredient at a zero-order rate of release comprising an active ingredient, a membrane controlling the rate of release of said active ingredient by diffusion through said membrane and a microporous reservoir material which is highly permeable to said active ingredient and in which said active ingredient is essentially insoluble, said microporous reservoir material having interconnected pores capable of retaining said active ingredient by capillary forces.

3. The controlled-release dispenser of claim 2 wherein the active ingredient is selected from pheromones, juvenile hormones, fragrances, insect attractants, insect repellants, perfumes, insecticides, fumigants, deodorizers, animal attractants, animal repellents and drugs.

4. The controlled-release dispenser of claim 3 wherein the active ingredient is a pheromone or insect attractant.

5. The controlled-release dispenser of claims 1 or 2 wherein the rate-controlling membrane is selected from polymers and copolymers of ethylene, propylene, ethylene/ethyl acrylate, ethylene/vinyl acetate, chlorinated ethylene, vinyl chloride, vinyl chloride/vinyl acetate, vinylidene chloride, ethylene terephthalate, ethylene/vinyl alcohol, ethylene/vinyl acetate/vinyl alcohol, ethylene/vinyloxyethanol, and styrene/acrylonitrile; rubbers of silicone, neoprene, butyl, and epichlorohydrin; polycarbonate; polyamides; polyimides; polyurethanes; and polyesters.

6. The controlled-release dispenser of claims 1 or 2 wherein the rate-controlling membrane is a polymer selected from polyethylenes, polyurethanes, polyesters, polyamides, polycarbonate, and vinyl polymers.

7. The controlled-release dispenser of claims 1 or 2 wherein the microporous reservoir material is selected from polysulfones, poly-tetrafluoroethylene, polycarbonate, polyurethanes, polyethylenes, and cellulose esters.

8. The controlled-release dispenser of claims 1 or 2 additionally containing anti-oxidants and/or ultraviolet light absorbers.

9. The controlled-release dispenser of claims 1 or 2 wherein a portion of the surface of the reservoir material is covered with a material that is essentially impermeable to the active ingredient.

10. A method of dispensing essentially all of an active ingredient selected from pheromones, insect attractants and insect repellants at a zero-order rate of release comprising loading a microporous reservoir material with said active ingredient, said microporous reservoir material being highly permeable to said active ingredient and in which said active ingredient is essentially insoluble, said microporous reservoir material having interconnected pores capable of retaining said active ingredient by capillary forces, and releasing said active ingredient by diffusion through a rate-controlling membrane.

11. The method of claim 10 wherein the rate-controlling membrane is a polymer selected from polyethylenes, polyurethanes, polyesters, polyamides, polycarbonate, and vinyl polymers.

12. The method of claim 10 wherein the microporous reservoir material is selected from polysulfones, polytetrafluoroethylene, polycarbonate, polyurethanes, polyethylenes, and cellulose esters.

* * * * *